US012678393B2

(12) United States Patent　　　(10) Patent No.:　US 12,678,393 B2
Kato　　　　　　　　　　　　　　　(45) Date of Patent:　　　Jul. 14, 2026

(54) MULTI-LAYER TYPE MAKEUP PROTECTION COSMETIC

(71) Applicant: KOSE CORPORATION, Tokyo (JP)

(72) Inventor: Kaoru Kato, Tokyo (JP)

(73) Assignee: KOSE CORPORATION, Tokyo (JP)

( * ) Notice: Subject to any disclaimer, the term of this patent is extended or adjusted under 35 U.S.C. 154(b) by 960 days.

(21) Appl. No.: 17/432,879

(22) PCT Filed: Feb. 21, 2020

(86) PCT No.: PCT/JP2020/007192

§ 371 (c)(1),
(2) Date: Aug. 20, 2021

(87) PCT Pub. No.: WO2020/175398

PCT Pub. Date: Sep. 3, 2020

(65) Prior Publication Data

US 2022/0192967 A1　　Jun. 23, 2022

(30) Foreign Application Priority Data

Feb. 27, 2019　　(JP) ................................. 2019-034450

(51) Int. Cl.
| *A61K 8/891* | (2006.01) |
| *A61K 8/04* | (2006.01) |
| *A61K 8/31* | (2006.01) |
| *A61K 8/58* | (2006.01) |
| *A61Q 1/00* | (2006.01) |

(52) U.S. Cl.
CPC .............. *A61K 8/891* (2013.01); *A61K 8/046* (2013.01); *A61K 8/31* (2013.01); *A61K 8/585* (2013.01); *A61Q 1/00* (2013.01)

(58) Field of Classification Search
None
See application file for complete search history.

(56) References Cited

U.S. PATENT DOCUMENTS

| 5,478,552 A | 12/1995 | Hasegawa ........................ 424/63 |
| 2007/0009446 A1* | 1/2007 | Romero ................. A61K 8/893 |
| | | 424/47 |
| 2009/0041683 A1* | 2/2009 | Molenda ................ A61K 8/585 |
| | | 424/47 |
| 2009/0041699 A1* | 2/2009 | Molenda ................ A61K 8/891 |
| | | 424/70.1 |
| 2010/0233114 A1* | 9/2010 | DeGeorge ................ A61Q 5/00 |
| | | 424/70.121 |
| 2013/0272995 A1* | 10/2013 | Hagiwara ............. C08F 130/08 |
| | | 526/279 |
| 2019/0290558 A1 | 9/2019 | Kang et al. |

FOREIGN PATENT DOCUMENTS

| CN | 107007479 A | 8/2017 |
| EP | 1632213 A1 | 3/2006 |
| EP | 2842544 A1 | 3/2015 |
| EP | 4 545 587 A1 | 4/2025 |
| JP | H 07-33625 A | 2/1995 |
| JP | 7-242528 A | 9/1995 |
| JP | H 07-242528 A | 9/1995 |
| JP | 7-267843 A | 10/1995 |
| JP | 2000-264824 A | 9/2000 |
| JP | 2001-187715 A | 7/2001 |
| JP | 2002-138030 A | 5/2002 |
| JP | 2006-306860 A | 11/2006 |
| JP | 2007-320905 A | 12/2007 |
| JP | 2009-500450 A | 1/2009 |
| JP | 2011-213669 A | 10/2011 |
| JP | 2012-180316 A | 9/2012 |
| JP | 2014-237615 A | 12/2014 |
| JP | 2018-008910 A | 1/2018 |
| JP | 2020-026401 A | 2/2020 |
| JP | 2024-002679 A | 1/2024 |
| KR | 10-2018-0062144 A | 6/2018 |
| WO | WO 2007/008458 A1 | 1/2007 |
| WO | WO 2016/001239 A1 | 1/2016 |
| WO | WO 2020/031921 A1 | 2/2020 |

OTHER PUBLICATIONS

Katie Schaefer "Trimethylsiloxysilicate Film-Formers for Hair/Skin Feel" <https://www.cosmeticsandtoiletries.com/cosmetic-ingredients/sensory/news/21842075/trimethylsiloxysilicate-film-formers-for-hair-skin-feel> (Year: 2011).*
L:oil Face Mist Official Website (original) & L:oil Face Mist Official Website(EN) (Internet Archive Date Nov. 16, 2016).
Make Keep Mist Kose Pre-release (original) & Make Keep Mist Kose Pre-release(EN) (Mar. 16, 2020).
Shake Mist product introduction site (original) & Shake Mist product introduction site (EN) (Internet Archive Date Apr. 9, 2019).
Korean Office Action dated Dec. 21, 2023, issued by the Korean Intellectual Property Office in corresponding application KR 10-2022-7039982.
European First Office Action mailed Jul. 14, 2023, issued to European Application No. 20763888.3.
Korean First Office Action mailed Feb. 2, 2021, issued to Korean Application No. 10-2021-7009861.
Pharmaceutical Food Examination No. 0524001, May 24, 2007, pp. 1-5.
About the display method of all ingredients of cosmetics, Mar. 6, 2001, Pharmaceutical Trial No. 163 / Pharmaceutical Supervision No. 220, pp. 1-3.

(Continued)

*Primary Examiner* — Nicole P Babson
(74) *Attorney, Agent, or Firm* — Stein IP, LLC

(57) ABSTRACT

A main object of the present technology is to provide a makeup protection cosmetic for use by spraying over makeup, which is a makeup protection cosmetic that is excellent in terms of the fineness of the mist upon use by spraying and yet has an excellent makeup protection effect. The present technology can provide a multi-layer makeup protection cosmetic for use by spraying over makeup, containing the following components (A) to (C): component (A): an oil-soluble film-forming agent, component (B): 40 to 95 mass % of water, and component (C): a volatile oil agent.

17 Claims, No Drawings

(56)         References Cited

OTHER PUBLICATIONS

Press release _ T-Garden, Oct. 21, 2015, Beauty oil mist that can be used on top of makeup L: oil-Royle—New release in all 3 types that can be selected according to your skin!, pp. 1-4.
Cosmetic-Info.jp, L: oil Face mist for oily skin, Oct. 20, 2015, pp. 1-2, https://www.cosmetic-info.jp/prod/detail.php?id=42134.
Notice of Dispatch of Duplicates of a Written Opposition, Jun. 22, 2022, Japanese Patent No. 6961124.
Extended European Search Report mailed Dec. 15, 2022, issued to European Application No. 20763888.3.
International Search Report mailed Mar. 24, 2020, issued to International Application No. PCT/JP2020/007192.
Notice of Reasons for Refusal mailed May 19, 2021, issued to Japanese Application No. 2021-502217.
Third Party Observation date Jun. 15, 2021, issued to International Application No. PCT/JP2020/007192.
Chinese Second Office Action dated Jun. 1, 2022, issued to the corresponding Chinese Application No. 202080006050.4.
Korean Final Rejection issued on Aug. 25, 2022, issued to Korean Application No. 10-2021-7009861.
Chinese First Office Action mailed Jan. 17, 2022, issued to Chinese Application No. 202080006050.4.
PCPC, Cetrimonium Chloride (Feb. 2021).
PCPC, Polysilicone-9 (Apr. 2, 2025).
PCPC, Polysilicone-9, Trade Names (2025).
Polymers, vol. 49, Future Hair Care and Polymers, Use of Polymers in Styling Products (Jan. 2000).
Kao—Functional Polymer Materials (May 9, 2025).
Kao—air structure-Hair knowledge (May 12, 2025).
Morphe: https://taylersedit.wordpress.com/2018/11/26/morphe-continuous-setting-mist-review/) put on the appendix 1 'Continuous Setting Mist' related internet home page, (Nov. 26, 2018.).
Explanation of the cosmetic ingredient labeling system, hosted by: Korea Food and Drug Administration Hosted by: Korea Cosmetics Association (2008).
Second Office Action mailed Jul. 1, 2024, issued to related Korean Application No. 10-2022-7039982.
Birth of "d Program Allerbarrier Mist" that protects the skin from airborne fine particles and dryness, Press Release, Jan. 21, 2018.
d Program Allergen Barrier Mist, Cosmetic-Info.jp, https://www.cosmetic-info.jp/prod/detail.php?id=55764.

* cited by examiner

MULTI-LAYER TYPE MAKEUP PROTECTION COSMETIC

CROSS-REFERENCE TO RELATED APPLICATIONS

This application is a National Stage Entry of PCT/JP2020/007192, filed on Feb. 21, 2020, in the Japanese Patent Office. This application claims the benefit of Japanese Patent Application No. JP 2019-034450, filed on Feb. 27, 2019, in the Japanese Patent Office. All disclosures of the document(s) named above are incorporated herein by reference.

TECHNICAL FIELD

The present technology relates to a makeup protection product, particularly to a makeup protection cosmetic for use by spraying onto the face.

BACKGROUND ART

For makeup cosmetics, there has been a strong desire to prevent smudging caused by sweat or rubbing against clothes, for example. Accordingly, a number of technologies for enhancing the makeup lasting effect of a cosmetic itself have been developed. However, some consumers have a strong desire to improve the lasting of makeup using their own cosmetics, or improve the lasting of their usual makeup, for example. In order to meet these demands, for the purpose of enhancing the lasting of makeup without causing smudging, protection cosmetics that can be used by applying over the face with makeup have been needed, and a cosmetic to be directly applied over makeup for the purpose of preventing smudging (Patent Literature 1) and the like have been developed in the past.

For example, Patent Literature 1 discloses that a method for providing an overcoat agent for preventing smudging, according to which secondary makeup is applied mainly to, among eye makeup cosmetics, cosmetics for eyes and eyebrows mainly used for eye edges, eyelashes, and eyebrows, such as eyeliners, mascaras, and eyebrow pencils, thereby achieving significant improvement in makeup durability and secondary adhesion, is provided.

In addition, Patent Literature 2 discloses to provide a mist cosmetic that is excellent in terms of the softness of the mist, moistness after application, compatibility, low squeakiness, and low stickiness.

In addition, Patent Literature 3 discloses to provide a skin cosmetic that has excellent long-term stability, does not let the foundation go patchy even when applied over the face with makeup, and is excellent in terms of a sense of moistness over time.

CITATION LIST

Patent Literature

Patent Literature 1: JP-A-2007-320905
Patent Literature 2: JP-A-2014-237615
Patent Literature 3: JP-A-2002-138030

SUMMARY OF INVENTION

Technical Problem

The present inventors have noted that there has conventionally been no attempt addressing the problem of providing a makeup protection cosmetic that achieves the fineness of the mist upon use by spraying and also has an excellent makeup protection effect (see, e.g., Patent Literatures 1 to 3). Thus, first, as shown below in [Examples], the present inventors have evaluated whether mist particles are unlikely to form water droplets on the skin upon use by spraying and also whether smudging is unlikely to occur after 8 hours from application, and tried to obtain a makeup protection product that is favorable in such evaluation.

Therefore, the present technology mainly addresses the problem of providing a makeup protection cosmetic for use by spraying over makeup, which is a makeup protection cosmetic that is excellent in terms of the fineness of the mist upon use by spraying and yet has an excellent makeup protection effect.

Solution to Problem

In such a situation, the present inventors have conducted extensive research to solve the above problem. As a result, they have found that when an oil-soluble film-forming agent, a specific amount of water, and a volatile oil agent are combined, a multi-layer makeup protection cosmetic that is excellent in terms of the fineness of the mist upon use by spraying and yet has an excellent makeup protection effect can be provided, and thus accomplished the present invention that can solve the above problem.

That is, the present invention is as follows.

[1] A multi-layer makeup protection cosmetic for use by spraying over makeup, including the following components (A) to (C):
(A) an oil-soluble film-forming agent;
(B) 40 to 95 mass % of water; and
(C) a volatile oil agent.

[2] The multi-layer makeup protection cosmetic according to [1] above, wherein the component (A) is a silicone-based film-forming agent.

[3] The multi-layer makeup protection cosmetic according to [1] or [2] above, wherein the component (A) contains trimethylsiloxysilicic acid.

[4] The multi-layer makeup protection cosmetic according to any one of [1] to [3] above, not including 0.25% or more of an emulsifier.

[5] The multi-layer makeup protection cosmetic according to any of [1] to [4] above, further including a silicone wax.

[6] The multi-layer makeup protection cosmetic according to any one of [1] to [5] above, for a spray container using no propellant.

Advantageous Effects of Invention

The present technology can provide a makeup protection cosmetic for use by spraying over makeup, which is a makeup protection cosmetic that is excellent in terms of the fineness of the mist upon use by spraying and yet has an excellent makeup protection effect. Incidentally, the effects described here are not necessarily limited, and any of the effects described herein may be applied.

DESCRIPTION OF EMBODIMENTS

Hereinafter, the present technology will be described in detail. Incidentally, the embodiments described hereinafter show examples of typical embodiments of the present technology, and do not narrow the interpretation of the scope of the present technology. In addition, unless otherwise noted, "%" herein expresses mass %, and a numerical range expressed using "to" is inclusive of both endpoints of the range. In addition, the upper limit and the lower limit of each numerical range can be arbitrarily combined as required.

<Overview of the Present Technology>

The present inventors have noted that when a makeup protection product is used by spraying over facial makeup, the user desires that smudging is hardly seen for as long as possible after spraying the product. In addition, the present inventors have noted that when the mist is fine upon use by spraying, such a product can be uniformly sprayed onto facial makeup without forming water droplets on the skin, making it easier to protect the makeup.

Thus, a first object of the present technology is to provide a makeup protection cosmetic for use by spraying over makeup, which is a makeup protection cosmetic that is excellent in terms of the fineness of the mist upon use by spraying and yet has an excellent makeup protection effect.

Further, a second object of the present technology is to provide a multi-layer makeup protection cosmetic for use by spraying over makeup, which has an excellent makeup protection effect and yet is excellent in terms of a low sense of burden, low stickiness, and the fineness of the mist upon use by spraying.

According to the present technology, the following components (A) to (C): (A) an oil-soluble film-forming agent, (B) 40 to 95 mass % of water, and (C) a volatile oil agent, are contained. As a result, the first object of the present technology, that is, to provide a makeup protection cosmetic which, when used by spraying over makeup, is excellent in terms of the fineness of the mist upon use by spraying and yet has an excellent makeup protection effect, can be achieved.

Further, in the present technology, in view of the fineness of the mist upon use by spraying and the makeup protection effect with high durability, it is preferable that the component (A) is a silicone-based film-forming agent. In addition, in view of the fineness of the mist upon use by spraying and the makeup protection effect with high durability, it is more preferable that the component (A) contains trimethylsiloxysilicic acid.

In addition, in the present technology, considering the usability for spraying over the face, it is preferable that the multi-layer makeup cosmetic is for a spray container using no propellant rather than an aerosol form using a propellant.

In addition, in the present technology, in view of the excellent makeup protection effect and the fineness of the mist upon use by spraying, and also in view of a low sense of burden and low stickiness, it is preferable that the multi-layer makeup protection cosmetic of the present technology further contains a silicon wax as a component (D). Further, in view of a low sense of burden and low stickiness, it is more preferable that 50 to 95 mass % of the component (B) water is contained in the cosmetic of the present technology.

Like this, according to the present technology, when the above components (A) to (D) are contained, the second object of the present technology, that is, to provide a multi-layer makeup protection cosmetic for use by spraying over makeup, which has an excellent makeup protection effect and yet is excellent in terms of a low sense of burden, low stickiness, and the fineness of the mist upon use by spraying, can be achieved.

<Component (A): Oil-Soluble Film-Forming Agent>

The component (A) oil-soluble film-forming agent used in the present technology may be any oil-soluble film-forming agent as long as it is soluble in an oil agent such as a volatile oil, forms a film, and is usable in ordinary cosmetics.

The component (A) oil-soluble film-forming agent is not particularly limited. For example, silicone-based resins such as trimethylsiloxysilicic acid, polymethylsilsesquioxane, acrylic-modified silicone, and fluorine-modified silicone; rosin acid-based resins such as rosin-modified phenolic resins and rosin esters; candelilla resin, vinyl acetate-based resins, polyvinyl isobutyl ether, polybutene, polyisobutylene; and like oil-soluble resins can be mentioned, and one or more kinds selected therefrom can be used. As a result, the fineness of the mist upon use by spraying and/or an excellent makeup protection effect can be obtained.

Commercially available products of the oil-soluble film-forming agent are not particularly limited. For example, KF7312J (solids content: 50%, solvent: cyclopentasiloxane, manufactured by Shin-Etsu Chemical Co., Ltd.), KF-9021 (solids content: 50%, solvent: cyclopentasiloxane, manufactured by Shin-Etsu Chemical Co., Ltd.), BY11-018 (solids content: 30%, solvent: cyclopentasiloxane, manufactured by Dow Corning Toray Co., Ltd.), KP541 (solids content: 60%, solvent: isopropanol, manufactured by Shin-Etsu Chemical Co., Ltd.), SR-1000 (manufactured by Momentive Performance Materials Japan LLC.), KP545 (solids content: 30%, solvent: cyclopentasiloxane, manufactured by Shin-Etsu Chemical Co., Ltd.), KP575 (solids content: 30%, solvent: cyclopentasiloxane, manufactured by Shin-Etsu Chemical Co. Ltd.), SILFORM FLEXIBLE RESIN (manufactured by Momentive Performance Materials Japan LLC.), XS66-B8226 (solids content: 50%, solvent: cyclopentasiloxane, manufactured by Momentive Performance Materials Japan LLC.), OPPANOL B-100 (manufactured by BASF SE), UNIFILMA HVY (manufactured by Chiba Flour Milling Co., Ltd.), and the like can be mentioned. One or more kinds selected therefrom can be used.

Among the component (A) oil-soluble film-forming agents, silicone-based resins are preferably used from the viewpoint that films that are resistant to sweat and sebum and have no stickiness can be more favorably formed. Among them, fluorine-modified silicone and/or trimethylsiloxysilicic acid are preferable, and among them, trimethylsiloxysilicic acid is still more preferable.

In the present technology, the content of the component (A) oil-soluble film-forming agent in the cosmetic of the present technology is not particularly limited. However, the preferred lower limit thereof is preferably 0.05% or more, more preferably 0.1% or more, still more preferably 0.5% or more, and yet more preferably 1% or more, while the preferred upper limit thereof is preferably 8% or less, more preferably 5% or less, still more preferably 4% or less, and yet more preferably 3% or less. As a result, the fineness of the mist upon use by spraying and/or an excellent makeup protection effect can be obtained.

Further, the preferred numerical range of the component (A) in the cosmetic of the present technology is preferably 0.1 to 5%, and more preferably 1 to 3%. Within this range, a makeup protection cosmetic that has a sufficient makeup protection effect and yet offers excellent comfort in use with an even lower sense of burden can be obtained.

Incidentally, the silicon-based resin content is not particularly limited. However, the preferred lower limit thereof in the content of the component (A) oil-soluble film-forming agent is preferably 50% or more, more preferably 80% or more, still more preferably 90% or more, yet more preferably 95% or more, more preferably 99% or more, and more preferably substantially 100%.

In addition, the silicon-based resin content in the cosmetic of the present technology is not particularly limited, but is preferably 0.1 to 5%, and more preferably 1 to 3%.

In addition, the trimethylsiloxysilicic acid content is not particularly limited. However, the preferred lower limit thereof in the silicon-based resin content is preferably 50% or more, more preferably 80% or more, still more preferably 90% or more, and yet more preferably 95% or more.

In addition, the trimethylsiloxysilicic acid content in the cosmetic of the present technology is preferably 0.1 to 5%, and more preferably 1 to 3%.

<Component (B): Water>

According to the present technology, water is contained as the component (B). As water, in addition to purified water, it is also possible to use ion exchange water, seawater, deep sea water, or steam-distilled plant water.

In the present technology, the content of the component (B) water is not particularly limited. However, the preferred lower limit thereof in the cosmetic of the present technology is 40% or more, more preferably 46% or more, still more preferably 50% or more, yet more preferably 55% or more, more preferably 60% or more, more preferably 65% or more, and more preferably 67% or more, while the preferred upper limit thereof is preferably 98% or less, more preferably 95% or less, still more preferably 90% or less, yet more preferably 85% or less, more preferably 80% or less, and more preferably 76% or less. As a result, the fineness of the mist upon use by spraying and/or an excellent makeup protection effect can be obtained.

Further, the preferred numerical range of the component (B) water in the cosmetic of the present technology is preferably 50 to 95%, but is more preferably 60 to 90%, and still more preferably 65 to 80%. Within this range, a makeup protection cosmetic that offers excellent comfort in use, which dries more quickly and has even lower stickiness, can be obtained.

<Component (C): Volatile Oil Agent>

The volatile oil agent as the component (C) used in the present technology is not particularly limited as long as it is liquid and volatile at 20° C. and normal pressure, and its viscosity or origin is not taken into consideration.

The volatile oil agent as the component (C) dissolves the component (A) oil-soluble film-forming agent, and also allows the same to be stably contained in the cosmetic.

Volatile oil agents as the component (C) are not particularly limited, and, for example, any of silicone-based oils, hydrocarbon-based oils, ester-based oils, and the like can be used. One or more kinds thereof can be used.

More specifically, for example, silicone-based oils such as low-molecular-weight methylpolysiloxanes, decamethyl cyclopentasiloxane, octamethyl cyclotetrasiloxane, dodeca-methyl cyclohexasiloxane, methyl trimethicone, decamethyl tetrasiloxane, and ethyl trisiloxane; hydrocarbon-based oils such as light liquid isoparaffin, isododecane, and isohexa-decane, and the like can be mentioned, but examples are not limited thereto. One or more kinds thereof can be used.

As commercially available products of volatile oil agents as the component (C), isopar H (manufactured by Esso Chemical Co., Ltd.), isododecane (manufactured by Bay-erAG), Isohexadecane (manufactured by Unigema), and iP Solvent 1620MU, IP Solvent 2028MU, and IP Solvent 2835 (all manufactured by Idemitsu Kosan Co., Ltd.) as light liquid isoparaffin; TSF405 (manufactured by Toshiba Sili-cone Co., Ltd.), SH245 and DC345 (manufactured by Dow Corning Toray Co., Ltd.), and KF-995 (manufactured by Shin-Etsu Chemical Co., Ltd.) as decamethyl cyclopentasi-loxane; Silicone TMF-1.5 (manufactured by Shin-Etsu Chemical Co., Ltd.) as methyl trimethicone; KF-96L-2CS (manufactured by Shin-Etsu Chemical Co. Ltd.) as low-molecular-weight methylpolysiloxane; KF-96L-1.5CS (manufactured by Shin-Etsu Chemical Co., Ltd.) as decam-ethyl tetrasiloxane; SILSOFT ETS (manufactured by Momentive Performance Materials Inc.) as ethyl trisiloxane; and the like can be mentioned. One or more kinds thereof can be used.

Among the component (C) volatile oil agents, in view of low stickiness, volatile silicone oils are preferable. More specifically, one or more kinds selected from decamethyl cyclopentasiloxane, methyl trimethicone, volatile dimeth-ylpolysiloxane (preferably dimethylpolysiloxane having a kinematic viscosity at 25° C. of 2 mm²/s or less), and the like are preferable. Incidentally, the kinematic viscosity (mm²/s) herein can be measured using the below-described Brook-field viscometer under its measurement conditions. The kinematic viscosity (mm²/s) can be calculated as viscosity (mPa·s)/density (g/cm³).

The content of the component (C) volatile oil agent in the present technology is not particularly limited. However, the preferred lower limit thereof in the cosmetic of the present technology is preferably 1% or more, more preferably 3% or more, still more preferably 4% or more, and yet more preferably 5% or more, while the preferred upper limit thereof is preferably 40% or less, more preferably 35% or less, still more preferably 30% or less, yet more preferably 25% or less, and more preferably 20% or less. As a result, the fineness of the mist upon use by spraying and/or an excellent makeup protection effect can be obtained.

The preferred numerical range of the component (C) volatile oil agent in the cosmetic of the present technology is preferably 5 to 40%, and more preferably 5 to 20%. Within this range, a multi-layer makeup protection cosmetic that offers excellent comfort in use, which dries more quickly and has even lower stickiness, can be obtained.

<Other Components>

In view of the fineness of the mist upon spraying and also in view of a clear interface, it is preferable that the multi-layer makeup protection cosmetic of the present technology contains substantially no emulsifier. In addition, in view of the lasting of makeup, it is preferable that the amount of emulsifier is small. Here, to contain substantially no emul-sifier means that the emulsifier content in the cosmetic of the present technology is less than 0.25%, preferably less than 0.1%, more preferably less than 0.05%, and most preferably zero. In other words, in view of emulsifier-free or emulsifier reduction, it is preferable that the multi-layer makeup cos-metic of the present technology does not contain an emul-sifier in an amount of 0.25% or more, preferably 0.1% or more, and more preferably 0.05% or more.

The multi-layer makeup protection cosmetic of the pres-ent technology may contain a wax that is usable in ordinary cosmetics. The wax may be synthetic or of natural origin, and commercially available products can be used. The wax preferably has a melting point of 25 to 60° C. The content of the wax is not particularly limited, but is preferably 0.1 to 5%, more preferably 0.1 to 3%, in the cosmetic of the present technology.

The wax is not particularly limited. For example, one or more kinds selected from hydrocarbon-based waxes, sili-cone waxes, natural waxes, and the like can be used. Further, among them, silicone waxes are preferable.

The multi-layer makeup protection cosmetic of the pres-ent technology preferably further contains a silicone wax.

The "silicone wax" used in the present technology is preferably a wax having a siloxane bond in the molecule, and any of water-soluble and oil-soluble waxes can be used as long as they are usable in ordinary cosmetics.

The silicon wax used in the present technology is not particularly limited. For example, alkyl-modified organopolysiloxanes, acrylic-modified organopolysiloxanes, higher fatty acid-modified organopolysiloxanes, higher alcohol-modified organopolysiloxanes, and the like can be mentioned, and one or more kinds selected therefrom can be used as necessary.

Commercially available products of the above silicone waxes are not particularly limited. For example, stearyl dimethicone, alkyl ($C_{26-28}$) dimethicone, stearoxy dimethicone, behenoxy dimethicone, (acrylates/stearyl acrylate/dimethicone methacrylate) copolymers, (acrylates/behenyl acrylate/dimethicone methacrylate) copolymers, (stearoxy methicone/dimethicone) copolymers, bisPEG-18 methyl ether dimethyl silane, and the like can be mentioned, but examples are not limited thereto. One or more kinds thereof can be used.

Among the silicone waxes described above, for the reason that excellent comfort in use with an even lower sense of burden and even lower stickiness is obtained, those having a melting point of 25 to 55° C. are preferable, those having a melting point of 25 to 40° C. are more preferable, and those having a melting point of 25 to 35° C. are still more preferable. Incidentally, the melting point can be measured by the Third Method described in the Japanese Standards of Quasi-drug Ingredients.

Commercially available products of the silicone wax are not particularly limited. For example, 2503 Cosmetic Wax and 2501 Cosmetic Wax (manufactured by Dow Corning Toray Co., Ltd.), SDM 5055 VP and CDM 3526 VP (manufactured by Wacker Asahikasei Silicone Co., Ltd.), KP-561P, KP-562P, and KF-7002 (manufactured by Shin-Etsu Chemical Co., Ltd.), ABIL Wax 2324, 2440, and 9800 (manufactured by Evonik Operations GmbH), and the like can be mentioned. One or more kinds thereof can be used.

The silicone wax can impart flexibility to a film of the component (A) oil-soluble film-forming agent, and can also reduce the sense of burden that the cosmetic gives to the skin.

Among the silicone waxes described above, acrylic-modified organopolysiloxanes are preferable, and among them, a graft copolymer composed of an acrylic polymer and dimethylpolysiloxane is preferable.

Among the silicone waxes described above, use of an (acrylates/stearyl acrylate/dimethicone methacrylate) copolymer allows for excellent comfort in use with even lower stickiness and thus is preferable.

The content of the silicon wax used in the present technology in the cosmetic of the present technology is not particularly limited. However, the preferred lower limit thereof is preferably 0.01% or more, more preferably 0.05% or more, and still more preferably 0.1% or more, while the preferred upper limit thereof is preferably 10% or less, more preferably 8% or less, yet more preferably 5% or less, and more preferably 3% or less. As a result, the fineness of the mist upon use by spraying and/or an excellent makeup protection effect can be obtained, and further excellent usability, that is, a low sense of burden and/or low stickiness, can be obtained.

Further, the preferred numerical range of the silicone wax in the cosmetic of the present technology is preferably 0.1 to 5%, and more preferably 0.1 to 3%. Within this range, a makeup protection cosmetic that is excellent in terms of a low sense of burden and is excellent in terms of low stickiness can be obtained.

Here, in the method of direct application onto the skin using a finger, etc., like the technique of Patent Literature 1, a force that drags the makeup film may be exerted, letting the makeup film go patchy or come off.

A mist cosmetic applied using a container with a spray nozzle, for example, can be sprayed/applied in the form of a mist without direct contact with the skin, and thus is an effective form in that application is possible without affecting the makeup film. As a makeup-lasting component used for mist cosmetics, for example, a method using a water-soluble polymer (Patent Literature 2) is known.

However, when a plant-derived or like water-soluble polymer is used, such a cosmetic tends to be insufficient in terms of low stickiness, the fineness of the mist, and the lasting of makeup. In addition, a method for enhancing the lasting of makeup using a water-soluble film-forming agent (Patent Literature 3), for example, has also been studied. However, use of a water-soluble film-forming agent may result in peculiar stickiness, slow drying, and a hard film, causing a sense of burden, and also may result in insufficient water repellency, causing vulnerability to sweat and the like.

Therefore, a second object of the present technology is to provide a cosmetic that can be applied without affecting makeup, has an excellent makeup lasting effect, and yet offers excellent comfort in use, including a low sense of burden, low stickiness, and the like.

The second object of the present technology can be achieved by a multi-layer makeup cosmetic according to a second embodiment of the present technology, further containing the silicone wax in addition to the above (A) to (C). In addition, according to the second embodiment of the present technology, even in the case where the silicone wax is contained and substantially no emulsifier is contained, and also even when used for a container with a spray nozzle using no propellant, the second object can be achieved.

In the multi-layer makeup protection cosmetic of the present invention, in addition to the above (A) to (C) and the above components, components used in ordinary cosmetics can be contained as necessary to the extent that the advantages of the present invention are not impaired. For example, waxes, surfactants (emulsifiers), oil-based components, water-based components, powders, moisturizers, thickeners, preservatives, UV absorbers, pH adjusters, fragrances, medicinal components, and the like can be mentioned. One or more kinds selected therefrom can be used.

As waxes, in addition to the silicone waxes described above, for example, hydrocarbon-based waxes such as (ethylene/propylene) copolymers, Fischer-Tropsch waxes, microcrystalline waxes, polyethylene waxes, ozokerite waxes, paraffin waxes, and ceresin waxes; natural waxes such as carnauba wax, beeswax, lanolin wax, and candelilla, and the like can be mentioned, but examples are not limited thereto. One or more kinds selected therefrom, including silicone waxes, can be used.

Water-soluble polymers are not particularly limited. For example, guar gum, sclerotium gum, gellan gum, pectin, agar, sodium chondroitin sulfate, hyaluronic acid, gum arabic, sodium alginate, carrageenan, xanthan gum, locust bean gum, methyl cellulose, hydroxyethyl cellulose, carboxymethyl cellulose, carboxyvinyl polymers, alkyl-modified carboxyvinyl polymers, polyvinyl alcohol, polyvinyl pyrrolidone, (sodium acrylate/sodium acryloyldimethyltaurine) copolymers, (PEG-240/decyltetradeceth-20/HDI) copolymers, and the like can be mentioned, and one or more kinds selected therefrom can be used.

Water-based components are not particularly limited. For example, glycerols such as glycerin, diglycerin, and polyglycerin; sugar alcohols such as sorbitol, maltitol, and glucose; lower alcohols such as ethanol and 1,3-butylene glycol, and the like can be mentioned, and one or more kinds selected therefrom can be used. In addition, a water-based component can also function as a solvent. Among them, lower alcohols (preferably $C_{13}$) are preferable.

In the cosmetic of the present technology, particularly when ethanol is contained, a refreshing feeling can be obtained upon use by spraying. Besides, the drying speed can be further improved, and excellent comfort in use with even lower stickiness can be obtained.

In this case, the content of the lower alcohols including ethanol is such that, in the cosmetic of the present technology, the preferred lower limit thereof is preferably 1% or more, more preferably 3% or more, and still more preferably 5% or more, while the preferred upper limit thereof is preferably 15% or less, and more preferably 13% or less.

In addition, the content of the ethanol is such that, in the cosmetic of the present technology, the preferred lower limit thereof is preferably 1% or more, more preferably 3% or more, and still more preferably 5% or more, while the preferred upper limit thereof is preferably 15% or less, and more preferably 10% or less.

Oil-based components are not limited in properties, and may be solid oils, semi-solid oils, liquid oils, and the like of animal oil origin, vegetable oil origin, synthetic oil origin, and the like generally used in cosmetic products. For example, hydrocarbons, fats and oils, hydrogenated oils, ester oils, fatty acids, non-volatile silicone oils, and the like can be mentioned. More specifically, hydrocarbons such as liquid paraffin, squalane, polyisobutylene, and polybutene, oils and fats such as olive oil, castor oil, and macadamia nut oil, esters such as cetyl isooctanate, isopropyl myristate, isopropyl palmitate, octyldodecyl myristate, and polyglyceryl diisostearate, fatty acids such as stearic acid, lauric acid, myristic acid, behenic acid, isostearic acid, and oleic acid, non-volatile silicone oils such as dimethylpolysiloxane and methylphenylpolysiloxane, essential oils, fragrances, and the like can be mentioned. One or more kinds selected therefrom can be used.

In the present technology, in view of further improvement in the fineness of the mist, it is preferable that a non-volatile silicone oils (preferably non-volatile dimethylpolysiloxane and/or non-volatile methylphenylpolysiloxane, etc.) are contained. In the case of using a silicone-based film-forming agent, in view of compatibility and also in view of further improvement in low stickiness, non-volatile dimethylpolysiloxane is preferable. In view of further improvement in the fineness of the mist, the kinematic viscosity of the non-volatile silicone oils at 25° C. is preferably 6 mm²/s or more, more preferably 6 to 20 mm²/s, and still more preferably 6 to 10 mm²/s. These ranges of the kinetic viscosity are also preferable from the viewpoint that the nozzle can be prevented from clogging after use. In addition, the preferred content of the non-volatile silicone oils in the cosmetic of the present technology is preferably 1 to 20 mass %, more preferably 3 to 15 mass %, and still more preferably 3 to 10 mass %.

Powders are not particularly limited as long as they are usable in ordinary cosmetics. For example, inorganic powders such as titanium oxide, zinc oxide, cerium oxide, aluminum oxide, silicic anhydride, calcium carbonate, chromium oxide, chromium hydroxide, iron blue, ultramarine blue, iron oxide, carbon black, mica, synthetic gold mica, sericite, talc, kaolin, barium sulfate, and boron nitride, nylon, polymethyl methacrylate, polyethylene, polypropylene, polystyrene, silicone resin powders, cellulose and derivatives thereof, urethane, silk powders, crystalline cellulose, N-acyl lysine, and the like, organic tar-based pigments such as Red No. 201, Red No. 202, Red No. 228, Orange No. 203, Blue No. 404, Yellow No. 401, Red No. 3, Red No. 104, Red No. 106, Orange No. 205, Yellow No. 4, Yellow No. 5, Green No. 3, Blue No. 1, Purple No. 401, and Purple No. 201, as well as pigment powders of these lake pigments, composite powders such as mica titanium, titanium oxide-coated mica titanium, zinc oxide-coated mica titanium, titanium oxide-coated glass powders, and carmine-coated mica titanium, laminated film powders such as polyethylene terephthalateialuminum/epoxy laminate powders and polyethylene terephthalateipolymethyl methacrylate laminate powders, and metal powders such as aluminum powders, gold, and silver can be mentioned. These powders may be surface-treated using one or more kinds of fluorine-based compounds, silicone-based compounds, metal soaps, lecithin, hydrogenated lecithin, collagen, amino acids, hydrocarbons, higher fatty acids, higher alcohols, esters, waxes, surfactants, and the like. One or more kinds selected therefrom can be used. When such a powder is contained, it is also possible to provide the multi-layer structure of the makeup protection cosmetic with three or more layers to the extent the advantages of the present invention are not impaired.

The powder content in the cosmetic of the present technology is not particularly limited. However, the preferred lower limit thereof is preferably 0.5% or more, and more preferably 1% or more, while the preferred upper limit thereof is preferably 10% or less, more preferably 5% or less, and still more preferably 3% or less.

As antioxidants, for example, α-tocopherol, ascorbic acid, and the like; as beauty ingredients, for example, vitamins, anti-inflammatories, crude drugs, and the like; and as preservatives, paraoxybenzoic acid esters, phenoxyethanol, alkanediol, chlorphenesin, and the like can be mentioned, but examples are not limited thereto, and one or more kinds thereof can be used. As pH adjusters, lactic acid, citric acid, glycolic acid, succinic acid, tartaric acid, malic acid, salts thereof, potassium carbonate, sodium hydrogen carbonate, ammonium hydrogen carbonate, and the like; and as refreshing agents, L-menthol, camphor, and the like can be mentioned, but examples are not limited thereto, and one or more kinds thereof can be suitably selected and used.

<Multi-Layer Makeup Protection Cosmetic of the Present Technology and Production Method Therefor>

The method for producing the multi-layer makeup protection cosmetic of the present technology is not particularly limited. The cosmetic can be produced by an ordinarily known method, and, for example, can be obtained by charging the components (A) to (C) and other components into a container (e.g., a container with a dispenser, a container with a spray nozzle, a spray container, a finger spray container, an accumulator spray container, a mist spray container, etc.). It is also possible that the components used in the present technology are mixed and then charged. In addition, the components used in the present technology may also be charged into a plurality of containers, such as a container for a water layer, a container for an oil layer, or their container and a container for a powder and provided as a two-component, three-component, or like multi-component product (kit). In the case of a multi-component product, the user can mix the water layer component, the oil layer component, the powder component, and the like in the desired ratio at the time of use, and then spray the mixture.

The multi-layer makeup protection cosmetic of the present technology is preferably used by spraying onto the face with base makeup such as foundation, or makeup such as eye shadow or blush. A container with a spray nozzle can be used, and use in the form of an aerosol is also possible. A spray container having a spray nozzle with a spray aperture (diameter) of approximately φ(diameter) 0.1 to 0.6 mm (preferably φ0.2 to 0.5 mm) may be used, and an aperture of φ0.3 mm may be used for spray evaluation. The cosmetic is for use by spraying, and thus is preferably a liquid cosmetic.

As shown below in [Examples], the makeup protection cosmetic of the present technology has a multi-layer structure having at least two layers including an upper oil layer and a lower water layer. The cosmetic can also contain a powder or the like and have three or more layers. Then, by mixing just before use by spraying, the multi-layer makeup protection cosmetic of the present technology can be favorably dispersed, and such a dispersed state can be maintained for a certain period of time. Meanwhile, when left for a certain period of time, it returns to the multi-layer structure.

Like this, the multi-layer makeup protection cosmetic of the present technology remains in a favorably dispersed state for a certain period of time after mixing, and thus mist-like fine particles can be sprayed. Further, according to the present technology, even in the form of a multi-layer structure including the component (B) water and the component (C) volatile oil agent, sprayability and film formability are excellent. This is attributable to the blending of the oil-soluble film-forming agent and also to the combination of the components (A) to (C). Further, according to the present technology, because the spray particles are fine even without blending an emulsifier, the cosmetic can also be provided as an emulsifier-free or low-emulsifier makeup protection cosmetic.

Moreover, according to the present technology, because of the combination of the components (A) to (C), a film with high water resistance and sebum resistance can be formed on the applied makeup, offering an excellent makeup protection effect with excellent durability. Further, according to the present technology, mist-like fine particles can be sprayed all over the face, and a film having high water resistance and water repellency can be formed all over the face. In addition, according to the present technology, the component (D) silicone wax may also be contained.

For such a reason, the protection cosmetic related to the present technology can form a film having an excellent barrier effect against pollen and air pollutant particles such as PM2.5 and yellow sand. Accordingly, the protection cosmetic related to the present technology can be used on the face with makeup for the purpose of blocking air pollution or as a measure against pollen or PM2.5, for example. The present technology is advantageous that various particles are less likely to adhere to the surface of makeup onto which protection cosmetic related to the present technology has been sprayed.

In addition, the viscosity (mPa·s) of the cosmetic of the present technology is preferably 1,500 mPa·s or less in 1-minute average measurement at 25° C. using a Brookfield viscometer with Rotor No. 2 at 6 rpm. Furthermore, the viscosity is more preferably 1,000 mPa·s or less because such a cosmetic is excellent in terms of the fineness of the mist.

EXAMPLES

Next, the present invention will be described in further detail with reference to test examples and examples, but the present invention is not limited thereto.

Test Examples 1 to 27: Multi-Layer Makeup Protection Cosmetic

Multi-layer makeup protection products having the compositions shown in Tables 1 to 4 were prepared by the following production method, and evaluated and judged according to the evaluation methods and judgment criteria shown below. The results are all shown in the tables.

TABLE 1

| | | | | | | (%) |
| Component Name | | Test Example 1 | Test Example 2 | Test Example 3 | Test Example 4 | Test Example 5 |
|---|---|---|---|---|---|---|
| (1) | Trimethylsiloxysilicic acid | 2 | 2 | 1 | 5 | 2 |
| (2) | Polymethylsilsesquioxane | — | — | — | — | — |
| (3) | (Acrylates/dimethicone) copolymer | — | — | — | — | — |
| (4) | Trifluoroalkyl dimethyl trimethylsiloxysilicic acid | — | — | — | — | — |
| (5) | (Styrene/acrylates) copolymer | — | — | — | — | — |
| (6) | (Cyclohexyl methacrylate/ethylhexyl methacrylate) copolymer | — | — | — | — | — |
| (7) | Dextrin isostearate (*1) | — | — | — | — | — |
| (8) | PVP | — | — | — | — | — |
| (9) | Xanthan gum | — | — | — | — | — |
| (10) | (Acrylates/stearyl acrylate/dimethicone methacrylate) copolymer (*2) | — | — | — | — | 0.5 |
| (11) | Stearyl dimethicone (*3) | — | — | — | — | — |
| (12) | BisPEG-18 methyl ether dimethylsilane (*4) | — | — | — | — | — |
| (13) | Paraffin wax (melting point: 45° C.) | — | 0.5 | — | — | — |
| (14) | Decamethyl cyclopentasiloxane | 10 | 10 | 10 | 10 | 35 |
| (15) | Dimethylpolysiloxane (25° C., 2 mm²/s) | — | — | — | — | — |
| (16) | Isododecane | — | — | — | — | — |
| (17) | Dimethylpolysiloxane (25° C., 6 mm²/s) | 5 | 5 | 5 | 5 | 5 |
| (18) | Polysorbate 80 | — | — | — | — | — |
| (19) | Fragrance | 0.05 | 0.05 | 0.05 | 0.05 | 0.05 |
| (20) | Purified water | Remaining amount | Remaining amount | Remaining amount | Remaining amount | Remaining amount |
| (21) | 1,3-Butylene glycol | 3 | 3 | 3 | 3 | 3 |
| (22) | Ethanol | 8 | 8 | 8 | 8 | 8 |
| (23) | Phenoxyethanol | 0.3 | 0.3 | 0.3 | 0.3 | 0.3 |
| (24) | Methylparaben | 0.1 | 0.1 | 0.1 | 0.1 | 0.1 |

TABLE 1-continued

| | Test Example 1 | Test Example 2 | Test Example 3 | Test Example 4 | Test Example 5 (%) |
|---|---|---|---|---|---|
| Component Name | | | | | |
| <Evaluation Items and Judgment Results> | | | | | |
| a. Fineness of Mist | ⊚ | ⊚ | ⊚ | ⊚ | ◯ |
| b. Makeup Protection Effect | ◯ | ◯ | ◯ | ◯ | ⊚ |
| c. Low Stickiness | X | X | Δ | X | X |
| d. Low Sense of Burden | Δ | X | ◯ | X | ◯ |

*1: UNIFILMA HVY (manufactured by Chiba Flour Milling Co., Ltd.)
*2: KP-561P (melting point: 25 to 35° C., manufactured by Shin-Etsu Chemical Co., Ltd.)
*3: DC2503 (melting point: 32° C., manufactured by Dow Corning Toray Co., Ltd.)
*4: 2501 Cosmetic Wax (melting point: 30° C., manufactured by Dow Corning Toray Co., Ltd.)

(Production Method)
   (A) Oil layer: (1) to (19) are uniformly heated and mixed.
   (B) Water layer: (20) to (24) are uniformly mixed.
   (C) The water layer of (B) and the oil layer of (A) were charged in this order into a container with a spray nozzle, thereby giving a multi-layer makeup protection product.

TABLE 2

| Component Name | Test Example 6 | Test Example 7 | Test Example 8 | Test Example 9 | Test Example 10 (%) |
|---|---|---|---|---|---|
| (1) Trimethylsiloxysilic acid | 0.1 | 2 | 5 | 2 | 2 |
| (2) Polymethylsilsesquioxane | — | — | — | — | — |
| (3) (Acrylates/dimethicone) copolymer | — | — | — | — | — |
| (4) Trifluoroalkyl dimethyl trimethylsiloxysilicic acid | — | — | — | — | — |
| (5) (Styrene/acrylates) copolymer | — | — | — | — | — |
| (6) (Cyclohexyl methacrylate/ethylhexyl methacrylate) copolymer | — | — | — | — | — |
| (7) Dextrin isostearate (*1) | — | — | — | — | — |
| (8) PVP | — | — | — | — | — |
| (9) Xanthan gum | — | — | — | — | — |
| (10) (Acrylates/stearyl acrylate/dimethicone methacrylate) copolymer (*2) | 0.5 | 0.5 | 0.5 | 0.1 | 5 |
| (11) Stearyl dimethicone (*3) | — | — | — | — | — |
| (12) BisPEG-18 methyl ether dimethylsilane (*4) | — | — | — | — | — |
| (13) Paraffin wax (melting point: 45° C.) | — | — | — | — | — |
| (14) Decamethyl cyclopentasiloxane | 10 | 10 | 10 | 10 | 10 |
| (15) Dimethylpolysiloxane (25° C., 2 mm²/s) | — | — | — | — | — |
| (16) Isododecane | — | — | — | — | — |
| (17) Dimethylpolysiloxane (25° C., 6 mm²/s) | 5 | 5 | 5 | 5 | 5 |
| (18) Polysorbate 80 | — | — | — | — | — |
| (19) Fragrance | 0.05 | 0.05 | 0.05 | 0.05 | 0.05 |
| (20) Purified water | Remaining amount | Remaining amount | Remaining amount | Remaining amount | Remaining amount |
| (21) 1,3-Buytene glycol | 3 | 3 | 3 | 3 | 3 |
| (22) Ethanol | 8 | 8 | 8 | 8 | 8 |
| (23) Phenoxyethanol | 0.3 | 0.3 | 0.3 | 0.3 | 0.3 |
| (24) Methylparaben | 0.1 | 0.1 | 0.1 | 0.1 | 0.1 |

TABLE 2-continued

| | | | | | |
|---|---|---|---|---|---|
| <Evaluation Items and Judgment Results> | | | | | |
| a. Fineness of Mist | ◎ | ◎ | ◎ | ◎ | ◎ |
| b. Makeup Protection Effect | ○ | ◎ | ◎ | ◎ | ◎ |
| c. Low Stickiness | ◎ | ◎ | ○ | ○ | ○ |
| d. Low Sense of Burden | ◎ | ◎ | ○ | ○ | ○ |

| | | | | | (%) |
|---|---|---|---|---|---|
| Component Name | Test Example 11 | Test Example 12 | Test Example 13 | Test Example 14 | Test Example 15 |
| (1) Trimethylsiloxysilic acid | — | — | — | — | — |
| (2) Polymethylsilsesquioxane | 2 | — | — | — | — |
| (3) (Acrylates/dimethicone) copolymer | — | 2 | — | — | — |
| (4) Trifluoroalkyl dimethyl trimethylsiloxysilicic acid | — | — | 2 | — | — |
| (5) (Styrene/acrylates) copolymer | — | — | — | 2 | — |
| (6) (Cyclohexyl methacrylate/ ethylhexyl methacrylate) copolymer | — | — | — | — | 2 |
| (7) Dextrin isostearate (*1) | — | — | — | — | — |
| (8) PVP | — | — | — | — | — |
| (9) Xanthan gum | — | — | — | — | — |
| (10) (Acrylates/stearyl acrylate/dimethicone methacrylate) copolymer (*2) | 0.5 | 0.5 | 0.5 | 0.5 | 0.5 |
| (11) Stearyl dimethicone (*3) | — | — | — | — | — |
| (12) BisPEG-18 methyl ether dimethylsilane (*4) | — | — | — | — | — |
| (13) Paraffin wax (melting point: 45° C.) | — | — | — | — | — |
| (14) Decamethyl cyclopentasiloxane | 10 | 10 | 10 | 10 | 10 |
| (15) Dimethylpolysiloxane (25° C., 2 mm$^2$/s) | — | — | — | — | — |
| (16) Isododecane | — | — | — | — | — |
| (17) Dimethylpolysiloxane (25° C., 6 mm$^2$/s) | 5 | 5 | 5 | 5 | 5 |
| (18) Polysorbate 80 | — | — | — | — | — |
| (19) Fragrance | 0.05 | 0.05 | 0.05 | 0.05 | 0.05 |
| (20) Purified water | Remaining amount | Remaining amount | Remaining amount | Remaining amount | Remaining amount |
| (21) 1,3-Buytene glycol | 3 | 3 | 3 | 3 | 3 |
| (22) Ethanol | 8 | 8 | 8 | 8 | 8 |
| (23) Phenoxyethanol | 0.3 | 0.3 | 0.3 | 0.3 | 0.3 |
| (24) Methylparaben | 0.1 | 0.1 | 0.1 | 0.1 | 0.1 |
| <Evaluation Items and Judgment Results> | | | | | |
| a. Fineness of Mist | ◎ | ◎ | ◎ | ◎ | ◎ |
| b. Makeup Protection Effect | ○ | ○ | ◎ | ○ | ○ |
| c. Low Stickiness | ◎ | ◎ | ◎ | ○ | ○ |
| d. Low Sense of Burden | ◎ | ◎ | ◎ | ◎ | ◎ |

TABLE 3

| | | | | | (%) |
|---|---|---|---|---|---|
| Component Name | Test Example 16 | Test Example 17 | Test Example 18 | Test Example 19 | Test Example 20 |
| (1) Trimethylsiloxysilic acid | — | 2 | 2 | 2 | 2 |
| (2) Polymethylsilsesquioxane | — | — | — | — | — |
| (3) (Acrylates/dimethicone) copolymer | — | — | — | — | — |
| (4) Trifluoroalkyl dimethyl trimethylsiloxysilicic acid | — | — | — | — | — |
| (5) (Styrene/acrylates) copolymer | — | — | — | — | — |
| (6) (Cyclohexyl methacrylate/ ethylhexyl methacrylate) copolymer | — | — | — | — | — |
| (7) Dextrin isostearate (*1) | 2 | — | — | — | — |
| (8) PVP | — | — | — | — | — |

TABLE 3-continued

| | | | | | |
|---|---|---|---|---|---|
| (9) Xanthan gum | — | — | — | — | — |
| (10) (Acrylates/stearyl acrylate/dimethicone methacrylate) copolymer (*2) | 0.5 | — | — | 0.5 | 0.5 |
| (11) Stearyl dimethicone (*3) | — | 0.5 | — | — | — |
| (12) BisPEG-18 methyl ether dimethylsilane (*4) | — | — | 0.5 | — | — |
| (13) Paraffin wax (melting point: 45° C.) | — | — | — | — | — |
| (14) Decamethyl cyclopentasiloxane | 10 | 10 | 10 | — | — |
| (15) Dimethylpolysiloxane (25° C., 2 mm$^2$/s) | — | — | — | 10 | — |
| (16) Isododecane | — | — | — | — | 10 |
| (17) Dimethylpolysiloxane (25° C., 6 mm$^2$/s) | 5 | 5 | 5 | 5 | 5 |
| (18) Polysorbate 80 | — | — | — | — | — |
| (19) Fragrance | 0.05 | 0.05 | 0.05 | 0.05 | 0.05 |
| (20) Purified water | Remaining amount | Remaining amount | Remaining amount | Remaining amount | Remaining amount |
| (21) 1,3-Buytene glycol | 3 | 3 | 3 | 3 | 3 |
| (22) Ethanol | 8 | 8 | 8 | 8 | 8 |
| (23) Phenoxyethanol | 0.3 | 0.3 | 0.3 | 0.3 | 0.3 |
| (24) Methylparaben | 0.1 | 0.1 | 0.1 | 0.1 | 0.1 |
| <Evaluation Items and Judgment Results> | | | | | |
| a. Fineness of Mist | ◎ | ◎ | ◎ | ◎ | ◎ |
| b. Makeup Protection Effect | ◎ | ◎ | ○ | ◎ | ◎ |
| c. Low Stickiness | ○ | ◎ | ◎ | ◎ | ◎ |
| d. Low Sense of Burden | ◎ | ◎ | ◎ | ◎ | ◎ |

(%)

| Component Name | Test Example 21 | Test Example 22 | Test Example 23 | Test Example 24 |
|---|---|---|---|---|
| (1) Trimethylsiloxysilic acid | 2 | 2 | 2 | 2 |
| (2) Polymethylsilsesquioxane | — | — | — | — |
| (3) (Acrylates/dimethicone) copolymer | — | — | — | — |
| (4) Trifluoroalkyl dimethyl trimethylsiloxysilicic acid | — | — | — | — |
| (5) (Styrene/acrylates) copolymer | — | — | — | — |
| (6) (Cyclohexyl methacrylate/ ethylhexyl methacrylate) copolymer | — | — | — | — |
| (7) Dextrin isostearate (*1) | — | — | — | — |
| (8) PVP | — | — | — | — |
| (9) Xanthan gum | — | — | — | — |
| (10) (Acrylates/stearyl acrylate/dimethicone methacrylate) copolymer (*2) | 0.5 | 0.5 | 0.5 | 0.5 |
| (11) Stearyl dimethicone (*3) | — | — | — | — |
| (12) BisPEG-18 methyl ether dimethylsilane (*4) | — | — | — | — |
| (13) Paraffin wax (melting point: 45° C.) | — | — | — | — |
| (14) Decamethyl cyclopentasiloxane | 10 | 10 | 10 | 4 |
| (15) Dimethylpolysiloxane (25° C., 2 mm$^2$/s) | — | — | — | — |
| (16) Isododecane | — | — | — | — |
| (17) Dimethylpolysiloxane (25° C., 6 mm$^2$/s) | 5 | 5 | 5 | 5 |
| (18) Polysorbate 80 | 0.2 | — | — | — |
| (19) Fragrance | 0.05 | 0.05 | 0.05 | 0.05 |
| (20) Purified water | Remaining amount | Remaining amount | Remaining amount | Remaining amount |
| (21) 1,3-Buytene glycol | 3 | 3 | 3 | 3 |
| (22) Ethanol | 8 | 15 | 3 | 8 |
| (23) Phenoxyethanol | 0.3 | 0.3 | 0.3 | 0.3 |
| (24) Methylparaben | 0.1 | 0.1 | 0.1 | 0.1 |

TABLE 3-continued

| <Evaluation Items and Judgment Results> | | | | |
|---|---|---|---|---|
| a. Fineness of Mist | ○ | ○ | ◎ | ○ |
| b. Makeup Protection Effect | ○ | ◎ | ◎ | ◎ |
| c. Low Stickiness | ○ | ◎ | ○ | ◎ |
| d. Low Sense of Burden | ◎ | ◎ | ◎ | ○ |

TABLE 4

| | | (%) | | |
|---|---|---|---|---|
| Component Name | | Test Example 25 | Test Example 26 | Test Example 27 |
| (1) | Trimethylsiloxysilicic acid | — | — | — |
| (2) | Polymethylsilsasquioxane | — | — | — |
| (3) | (Acrylate/dimethicone) copolymer | — | — | — |
| (4) | Trifluoroalkyl dimethyl trimethylsiloxysilicic acid | — | — | — |
| (5) | (Styrene/acrylates) copolymer | — | — | — |
| (6) | (Cyclohexyl methacrylate/ethylhexyl methacrylate) copolymer | — | — | — |
| (7) | Dextrin isostearate (*1) | — | — | — |
| (8) | PVP | — | 2 | — |
| (9) | Xanthan gum | — | — | 2 |
| (10) | (Acrylates/stearyl acrylate/dimethicone methacrylate) copolymer (*2) | 0.5 | 0.5 | 0.5 |
| (11) | Stearyl dimethicone (*3) | — | — | — |
| (12) | BisPEG-18 methyl ether dimethylsilane (*4) | — | — | — |
| (13) | Paraffin wax (melting point: 45° C.) | — | — | — |
| (14) | Decamethyl cyclopentasiloxane | 10 | 10 | 10 |
| (15) | Dimethylpolysiloxane (25° C., 2 mm$^2$/s) | — | — | — |
| (16) | Isododecane | — | — | — |
| (17) | Dimethylpolysiloxane (25° C., 6 mm$^2$/s) | 5 | 5 | 5 |
| (18) | Polysorbate 80 | — | — | — |
| (19) | Fragrance | 0.05 | 0.05 | 0.05 |
| (20) | Purified water | Remaining amount | Remaining amount | Remaining amount |
| (21) | 1,3-Butylene glycol | 3 | 3 | 3 |
| (22) | Ethanol | 8 | 8 | 8 |
| (23) | Phenoxyethanol | 0.3 | 0.3 | 0.3 |
| (24) | Methylparaben | 0.1 | 0.1 | 0.1 |
| <Evaluation Items and Judgment Results> | | | | |
| a. Fineness of Mist | | ◎ | ◎ | ◎ |
| b. Makeup Protection Effect | | X | Δ | X |
| c. Low Stickiness | | ◎ | X | X |
| d. Low Sense of Burden | | ◎ | X | ◎ |

(Evaluation Method)

Ten special panelists for cosmetic product evaluation used each of the multi-layer makeup protection products of the test examples. The product was sprayed five times all over the face with makeup (foundation and eye makeup), and "a. fineness of the mist", "b. makeup protection effect", "c. low stickiness", and "d. a low sense of burden" were evaluated and scored on a 5-point scale according to the following evaluation criteria. With respect to the items a. to c., evaluation was made during and immediately after use. With respect to "b. makeup protection effect", the panelists led normal lives after use, and, after 8 hours, the lasting of makeup was evaluated. Subsequently, the average score of all the panelists was calculated, and judgement was made according to the following judgement criteria.

[Evaluation Criteria]

a. Fineness of Mist

[Score]: [Evaluation Results]

4: Mist particles are extremely fine.

3: Mist particles are moderately fine.

2: Mist particles are slightly large.

1: Mist particles are large and form water droplets on the skin.

0: Not discharged in mist form.

b. Makeup Protection Effect

[Score]: [Evaluation Results]

4: After 8 hours from application, no smudging is seen at all.

3: After 8 hours from application, almost no smudging is seen.

2: After 8 hours from application, slight smudging is seen.

1: After 8 hours from application, smudging is seen.

0: After 8 hours from application, extreme smudging is seen.

c. Lack of Stickiness

[Score]: [Evaluation Results]

4: Not sticky at all.

3: Almost not sticky.

2: Neither.

1: Slightly sticky.

0: Extremely sticky.

d. Low Sense of Burden

[Score]: [Evaluation Results]

4: No sense of burden at all.

3: Almost no sense of burden.

2: Neither.

1: Slight sense of burden.

0: Extreme sense of burden.

[Judgement Criteria]

| [Average Score]: | [Judgment] |
|---|---|
| 3.5 or more: | ◉ (Excellent) |
| 2.5 or more to less than 3.5: | ○ (Good) |
| 1.0 or more and less than 2.5: | Δ (Slightly poor) |
| Less than 1.0: | X (Poor) |

The multi-layer makeup protection products of Test Examples 1 to 27 each had a multi-layer structure having two layers, that is, an upper oil layer and a lower water layer.

As is clear from the results in the tables, the multi-layer makeup protection products of Test Examples 1 to 24 according to the present technology were, because (A) an oil-soluble film-forming agent, (B) 40% or more of water, and (C) a volatile oil agent were contained, excellent in terms of both the fineness of the mist upon spraying and the makeup protection effect. Then, the cosmetics of the present technology were each sprayed in the form of a fine mist softly all over the face and did not spoil the applied makeup. Incidentally, the spray aperture of the container with a spray nozzle is φ0.3 mm.

In addition, from the evaluation results of the cosmetics of the present technology (Test Examples 1 to 24), the cosmetics of the present technology can be sprayed in the form of a fine mist all over the face with makeup, and therefore, it is easy even for a general user to form a makeup film uniformly on the entire face with an appropriate film thickness. In addition, use of the cosmetic of the present technology has an excellent advantage in that even by a general user, a makeup film with high water repellency and oil repellency can be easily formed on makeup, and its makeup protection effect is also high.

In addition, the cosmetics of the present technology (Test Examples 1 to 24) do not cause smudging for as long as 8 hours after application, and thus the cosmetics of the present technology are advantageous in that they have high sebum resistance.

Incidentally, the contact angle measurement device and measurement method were as follows.

Measurement equipment: Fully Automatic Contact Angle Meter DM-500, manufactured by Kyowa Interface Science Co., Ltd.

Coating film preparation method: A 30% film-forming agent solution is applied onto a glass plate manufactured by Toshin Riko Co., Ltd. (thickness: 3 mm, dimension: 70 mm×120 mm) to form a film with a thickness of 400 μm, and dried at 70° C. for 10 hours to prepare a coating film.

Dropped sample: Purified water is used to confirm water repellency, and triethylhexanoin is used to confirm oil repellency.

Contact angle measurement method: Purified water: 2 μL or triethylhexanoin: 1 μL is dropped onto a coating film, then the contact angle after 500 ms (milliseconds) is measured five times, and the average is calculated.

Films of the oil-soluble film-forming agents used in the cosmetics of the present technology (Test Examples 1 to 24) have high contact angles with respect to both water and an oil agent, showing that they have high water resistance/water repellency and oil resistance/oil repellency. According to the present technology, the cosmetic is in the form of a fine mist and can form a uniform makeup film, and thus is likely to favorably exhibit such properties.

Further, in the multi-layer makeup protection products of Test Examples 6 to 24 according to the present technology, because a silicone wax was further blended to the components (A) to (C), as compared with the multi-layer makeup cosmetics of Test Examples 1 to 5, the effects obtained were even more favorable also in terms of usability, that is, low stickiness and a low sense of burden on the skin. Accordingly, the multi-layer makeup protection cosmetics (films thereof) containing the components (A) to (D) according to the present technology were excellent in terms of all the items, that is, the fineness of the mist upon spraying, the makeup protection effect, low stickiness, and a low sense of burden on the skin. The cosmetics containing the components (A) to (D) of the present technology were each sprayed in the form of a fine mist softly all over the face and did not spoil the applied makeup. In addition, in the case where the cosmetic of the present technology contains the components (A) to (D), in view of improving low stickiness, it is preferable that the content of water as the component (B) is at least 50% or more.

In addition, in the multi-layer makeup cosmetics (Test Examples 1 to 24) according to the present technology, even without blending an emulsifier, it was possible for each cosmetic to be sprayed in the form of a fine mist softly all over the face by pressing the spray part with a finger.

In addition, in the multi-layer makeup cosmetics (Test Examples 1 to 24) according to the present technology, the viscosities (25° C.; Brookfield viscometer) according to the above viscosity measurement method were 1,000 mPa·s or less.

In contrast, in all of Test Examples 25 to 27 where no component (A) oil-soluble film-forming agent was contained, the makeup protection effect was inferior. Further, in Test Examples 26 and 27 where, of the components (A) to (D), the component (A) oil-soluble film-forming agent was replaced with a water-soluble film-forming agent, the makeup protection effect and low stickiness were significantly impaired.

| Formulation Example 1: Two-Layer Makeup Protection Lotion | |
|---|---|
| (Component) | (%) |
| 1. Olive oil | 5 |
| 2. Polymethylsilsesquioxane (*5) | 1.2 |
| 3. Dimethylpolysiloxane (*6) | 10 |
| 4. Ethanol | 3 |
| 5. Isotridecyl isononanoate | 1.5 |
| 6. Pentaerythrityl tetraethylhexanoate (*7) | 1.5 |
| 7. Tocopherol | 0.006 |
| 8. Fragrance | 0.15 |
| 9. Cetyl 2-ethylhexanoate | 5 |
| 10. Ethanol | 7 |
| 11. 1,3-Butylene glycol | 2.1 |
| 12. BisPEG-18 methyl ether dimethylsilane (*4) | 7 |
| 13. Sodium hyaluronate (*8) | 0.1 |
| 14. Collagen (*9) | 0.1 |
| 15. Sodium chloride | 0.7 |
| 16. Sodium monohydrogen phosphate | 0.07 |
| 17. Sodium dihydrogen phosphate | 0.07 |
| 18. Purified water | Remaining amount |

*5: SilForm Flexible Resin (manufactured by Momentive Performance Materials Japan LLC.)
*6: KF-96L-2CS (25° C.: 2 mm²/s, manufactured by Shin-Etsu Chemical Co., Ltd.)
*7: SALACOS 5408 (manufactured by Nisshin OilliO Group, Ltd.)
*8: Hyaluronic acid FCH201 (manufactured by Kikkoman Biochemifa Company)
*9: PANCOGEN MARINE (manufactured by GATTEFOSSE)

(Production Method)

(A) Oil layer: Components (1) to (9) are heated and uniformly mixed.

(B) Water layer: Components (10) to (18) are uniformly mixed.

(C) The water layer of (B) and the oil layer of (A) were charged in this order into a container with a spray nozzle (φ0.3 mm) to give a two-layer makeup protection lotion.

The two-layer makeup protection lotion of Formulation Example 1 thus obtained, which is a product of the present technology, was excellent in terms of the fineness of the mist upon spraying, the quickness of drying after spraying, low stickiness, a low sense of burden on the skin, and the makeup protection effect. After being left to stand for a while, the cosmetic turns into two layers, that is, an oil layer and a water layer, and can be mixed upon use and sprayed. The viscosity (25° C.; Brookfield viscometer) of Formulation Example 1 according to the above viscosity measurement method was 1,000 mPa·s or less.

| Formulation Example 2: Makeup Keeping Spray | |
| --- | --- |
| (Component) | (%) |
| 1. Trimethylsiloxysilicic acid (*10) | 1.5 |
| 2. (Acrylates/behenyl acrylate/dimethicone methacrylate) copolymer (*11) | 0.3 |
| 3. Decamethyl cyclopentasiloxane | 20 |
| 4. Isononyl isononanoate | 3 |
| 5. Ethylhexyl methoxycinnamate | 5 |
| 6. Fragrance | 0.15 |
| 7. Macadamia nut oil | 0.15 |
| 8. Argania spinosa kernel oil | 0.15 |
| 9. L-serine | 0.35 |
| 10. 1,3-Butylene glycol | 3.5 |
| 11. Purified water | Remaining amount |
| 12. Ethanol | 5 |

*10: Kf-9021 (50% cyclopentasiloxane solution, manufactured by Shin-Etsu Chemical Co., Ltd.)
*11: KP-562P (melting point: 45 to 55° C., manufactured by Shin-Etsu Chemical Co., Ltd.)

(Production Method)

(A) Oil layer: Components (1) to (8) are heated and uniformly mixed.

(B) Water layer: Components (9) to (12) are uniformly mixed.

(C) The oil layer of (A) and the water layer of (B) are mixed to give a stock solution.

(D) To 45 parts of the stock solution of (C), 55 parts of a propellant (dimethyl ether) was added and charged into in an aerosol container to give a makeup keeping spray.

The makeup keeping spray of Formulation Example 2, which is a product of the present technology, was excellent in terms of the fineness of the mist upon spraying, low stickiness, a low sense of burden on the skin, and the makeup protection effect. After being left to stand for a while, the cosmetic turns into two layers, that is, an oil layer and a water layer, and can be mixed upon use and sprayed. The viscosity (25° C.; Brookfield viscometer) of Formulation Example 2 according to the above viscosity measurement method was 1,000 mPa·s or less.

| Formulation Example 3: Two-Layer Makeup-Keeping Protection Cosmetic | |
| --- | --- |
| (Component) | (%) |
| 1. Meadowfoam oil | 1 |
| 2. Macadamia nut oil | 1 |
| 3. Rice bran oil | 1 |
| 4. Tri(caprylic/capric acid) glyceryl | 2 |
| 5. (Acrylates/dimethicone) copolymer (*12) | 12.5 |
| 6. Stearyl dimethicone (*3) | 3 |
| 7. Dimethylpolysiloxane (*14) | 5 |
| 8. Methyl trimethicone | 5 |
| 9. Ethanol | 5 |
| 10. Astaxanthin (*15) | 0.1 |
| 11. Tocopherol | 0.01 |
| 12. Fragrance | 0.1 |
| 13. Cetyl 2-ethylhexanoate | 7.2 |
| 14. Ethanol | 6 |
| 15. Humus extract | 0.1 |
| 16. Hamamelis extract | 0.1 |
| 17. Sodium chloride | 0.4 |
| 18. Citric acid | 0.01 |
| 19. Sodium citrate | 0.008 |
| 20. Purified water | Remaining amount |

*12: KP-549 (40% solids content methyl trimethicone solution, manufactured by Shin-Etsu Chemical Co., Ltd.)
*14: KF-96L-1.5CS (25° C.: 1.5 mm²/s, manufactured by Shin-Etsu Chemical Co., Ltd.)
*15: Astaxanthin-5C (manufactured by Oryza Oil&Fat Chemical Co., Ltd.)

(Production Method)

(A) Oil layer: Components (1) to (13) are heated and uniformly mixed.

(B) Water layer: Components (14) to (20) are uniformly mixed.

(C) The oil layer of (A) and the water layer of (B) were charged into a container with a spray nozzle (φ0.3 mm) to give a two-layer makeup-keeping protection cosmetic.

The two-layer makeup-keeping protection cosmetic of Formulation Example 3, which is a product of the present technology, was excellent in terms of the fineness of the mist upon spraying, low stickiness, a low sense of burden on the skin, and the makeup protection effect. After being left to stand for a while, the cosmetic turns into two layers, that is, an oil layer and a water layer, and can be mixed upon use and sprayed. The viscosity (25° C.; Brookfield viscometer) of Formulation Example 3 according to the above viscosity measurement method was 1,000 mPa·s or less.

| Formulation Example 4: Multi-Layer Makeup Protection Cosmetic (Overcoat Mist) | |
| --- | --- |
| (Component) | (%) |
| 1. Isohexadecane | 2 |
| 2. Hydrogenated polydecene | 1 |
| 3. Trimethylsiloxysilicic acid | 2 |
| 4. Isotridecyl isononanoate | 1 |
| 5. Tocopherol | 0.004 |
| 6. Fragrance | 0.1 |
| 7. Purple No. 201 | 0.01 |
| 8. Red No. 218 | 0.01 |
| 9. Dimethylpolysiloxane(*6) | 14 |
| 10. Ethanol | 7 |
| 11. Glycerin | 3.5 |
| 12. 1,3-Butylene glycol | 3.5 |
| 13. BisPEG-18 methyl ether dimethylsilane (*4) | 3.5 |
| 14. Sodium chloride | 0.7 |
| 15. Sodium lactate | 0.07 |
| 16. Lactic acid | 0.07 |
| 17. Blue No. 1 | 0.02 |
| 18. Purple No. 401 | 0.007 |

-continued

Formulation Example 4: Multi-Layer Makeup
Protection Cosmetic (Overcoat Mist)

| (Component) | (%) |
|---|---|
| 19. Purified water | Remaining amount |
| 20. Silica (*16) | 2 |
| 21. Kaolin (*17) | 2 |
| 22. (HDI/PPG/polycaprolactone) cross-polymer (*18) | 2 |
| 23. Crystalline cellulose (*19) | 4 |

*16: Silica Microbeads P-1505 (manufactured by JGC Catalysts and Chemicals Ltd.)
*17: Japanese Pharmacopoeia Kaolin (JP100) (manufactured by Takehara Kagaku Kogyo Co., Ltd.)
*18: CS-400 (manufactured by Negami Chemical Industrial Co., Ltd.)
*19: CEOLUS PH-F20JP (manufactured by Asahi Kasei Chemicals Corporation)

(Production Method)
    (A) Oil layer: Components (1) to (9) were heated and uniformly mixed.
    (B) Water layer: Components (10) to (19) are uniformly mixed.
    (C) Powder layer: Components (20) to (23) are uniformly mixed.
    (D) The oil layer of (A), the water layer of (B), and the powder layer of (C) were charged into a container with a spray nozzle ($\varphi > 0.3$ mm) to give a multi-layer makeup protection cosmetic (overcoat mist).

The multi-layer makeup protection cosmetic (overcoat mist) of Formulation Example 4 thus obtained, which is a product of the present technology, was excellent in terms of the fineness of the mist upon spraying, low stickiness, a low sense of burden on the skin, and the makeup protection effect. After being left to stand for a while, the cosmetic turns into three layers, that is, an oil layer, a water layer, and a powder layer, and can be mixed upon use and sprayed. The viscosity (25° C.; Brookfield viscometer) of Formulation Example 4 according to the above viscosity measurement method was 1,000 mPa·s or less.

Formulation Example 5: Multi-Layer Makeup
Protection Cosmetic (Overcoat Mist)

| (Component) | (%) |
|---|---|
| 1. Trimethylsiloxysilicic acid | 4 |
| 2. Ethylhexyl methoxycinnamate | 5 |
| 3. Dimethylpolysiloxane (*6) | 5 |
| 4. Dimethylpolysiloxane (*20) | 5 |
| 5. Decamethyl cyclopentasiloxane | 5 |
| 6. Diphenylsiloxyphenyl trimethicone | 3 |
| 7. Fragrance | 0.15 |
| 8. Niacinamide | 2 |
| 9. Menthol | 0.5 |
| 10. 1,3-Butylene glycol | 5 |
| 11. Purified water | Remaining amount |
| 12. Ethanol | 10 |
| 13. Titanium oxide (average particle size: 0.035 μm) (*21) | 1 |
| 14. Titanium oxide (average particle size: 0.25 μm) | 2 |
| 15. Zinc oxide (average particle size: 0.025 μm) (*22) | 2 |

*20: KF-96A-6CS (25° C.: 6 mm²/s, manufactured by Shin-Etsu Chemical Co., Ltd.)
*21: SMT-500SAS (average particle size: 0.035 μm, manufactured by TAYCA Corporation)
*22: MZ-500 (average particle size: 0.025 μm, manufactured by TAYCA Corporation)

(Production Method)
    (A) Oil layer: Components (1) to (7) were heated and uniformly mixed.
    (B) Water layer: Components (8) to (12) are uniformly mixed.

(C) Powder layer: Components (13) to (15) are uniformly mixed.
    (D) The oil layer of (A), the water layer of (B), and the powder layer of (C) were charged into a container with a spray nozzle ($\varphi 0.3$ mm) to give a multi-layer makeup protection cosmetic (overcoat mist).

The multi-layer makeup protection cosmetic (overcoat mist) of Formulation Example 5 thus obtained, which is a product of the present technology, was excellent in terms of the fineness of the mist upon spraying, low stickiness, a low sense of burden on the skin, and the makeup protection effect. After being left to stand for a while, the cosmetic turns into three layers, that is, an oil layer, a water layer, and a powder layer, and can be mixed upon use and sprayed. The viscosity (25° C.; Brookfield viscometer) of Formulation Example 5 according to the above viscosity measurement method was 1,000 mPa·s or less. In addition, because a non-volatile silicone oil having a kinematic viscosity at 25° C. of 6 to 10 mm²/s was blended, nozzle clogging after use was prevented, allowing the cosmetic to be smoothly sprayed upon re-spraying.

Formulation Example 6: Multi-layer Makeup Protection Cosmetic

| (Component) | (%) |
|---|---|
| Oil Layer | |
| 1. Trifluoroalkyl dimethyl trimethylsiloxysilicic acid (*22) | 5 |
| 2. Dimethylpolysiloxane | 6 |
| 3. Isododecane | Remaining amount |
| 4. Olive oil | 5 |
| 5. Tocopherol | 1 |
| 6. Fragrance | 3 |
| Water Layer | |
| 1. Rice fermented liquid | 0.5 |
| 2. 1,3-Butylene glycol | 5 |
| 3. Purified water | Remaining amount |
| 4. Ethanol | 10 |

*22: XS66-B8226 (manufactured by Momentive Performance Materials Japan LLC.)

(Production Method)
    (A) Oil layer: Components (1) to (6) are heated, uniformly mixed, cooled, and then charged into a container.
    (B) Water layer: Components (1) to (4) were uniformly mixed and charged into a container,
    (C) At the time of use, (A) and (B) were mixed within a range of (A):(B)=5:5 to 1:9 depending on the preference in a container with a spray nozzle ($\varphi > 0.2$ mm) to give a multi-layer makeup protection cosmetic.

The multi-layer makeup protection cosmetic of Formulation Example 6 thus obtained, which is a product of the present technology, was excellent in terms of the fineness of the mist upon spraying and the makeup protection effect. After being left to stand for a while, the cosmetic turns into two layers, that is, an oil layer and a water layer, and can be mixed upon use and sprayed. The viscosity (25° C.; Brookfield viscometer) of Formulation Example 6 according to the above viscosity measurement method was 1,000 mPa·s or less.

The invention claimed is:
    1. A multi-layer makeup protection cosmetic for use by spraying over makeup, comprising the following components (A) to (C):

(A) 0.1 to 8 mass % of an oil-soluble film-forming agent;

(B) 50 to 98 mass % or more of water; and (C) a volatile oil agent, and wherein the multi-lager makeup protection cosmetic comprises less than 0.05 mass % of a cationic emulsifier or comprises no cationic emulsifier.

2. The multi-layer makeup protection cosmetic according to claim 1, wherein the component (A) is a silicone-based film-forming agent.

3. The multi-layer makeup protection cosmetic according to claim 1, wherein the component (A) comprises trimethylsiloxysilicic acid.

4. The multi-layer makeup protection cosmetic according to claim 1, further comprising a silicone wax.

5. The multi-layer makeup protection cosmetic according to claim 1, wherein said multi-layer makeup protection cosmetic is formulated inside of a spray container, and wherein the spray container comprises no propellant.

6. The multi-layer makeup protection cosmetic according to claim 4, wherein said multi-layer makeup protection cosmetic is formulated inside of a spray container and wherein the spray container comprises no propellant.

7. The multi-layer makeup protection cosmetic according to claim 1, wherein the multi-layer makeup protection cosmetic comprises 0.1% to 5% of the component (A).

8. The multi-layer makeup protection cosmetic according to claim 1, wherein the multi-layer makeup protection cosmetic comprises 1% to 40% of the component (C).

9. The multi-layer makeup protection cosmetic according to claim 1, wherein the multi-layer makeup protection cosmetic comprises 5% to 40% of the component (C).

10. The multi-layer makeup protection cosmetic according to claim 4, wherein the multi-layer makeup protection cosmetic comprises 1% to 40% of the component (C).

11. The multi-layer makeup protection cosmetic according to claim 1, wherein the component (C) is selected from one or more of the group consisting of: silicone-based oils and hydrocarbon-based oils.

12. The multi-layer makeup protection cosmetic according to claim 1, wherein said multi-layer makeup protection cosmetic comprises no cationic emulsifier.

13. The multi-layer makeup protection cosmetic according to claim 12, further comprising a silicone wax.

14. A multi-layer makeup protection cosmetic for use by spraying over makeup, comprising the following components (A) to (C):

(A) 0.1 to 8 mass % of an oil-soluble film-forming agent;

(B) 50 to 98 mass % or more of water; and (C) a volatile oil agent, and wherein the multi-layer makeup protection cosmetic comprises less than 0.05 mass % of an emulsifier or comprises no emulsifier.

15. The multi-layer makeup protection cosmetic according to claim 14, wherein said multi-layer makeup protection cosmetic does not comprise the emulsifier.

16. The multi-layer makeup protection cosmetic according to claim 14, further comprising a silicone wax.

17. The multi-layer makeup protection cosmetic according to claim 15, further comprising a silicone wax.

* * * * *